US012685497B2

(12) United States Patent
Li

(10) Patent No.: US 12,685,497 B2
(45) Date of Patent: Jul. 21, 2026

(54) SYSTEMS, APPARATUSES, AND METHODS FOR DATA ACQUISITION IN PET

(71) Applicant: SHANGHAI UNITED IMAGING HEALTHCARE CO., LTD., Shanghai (CN)

(72) Inventor: Jun Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 362 days.

(21) Appl. No.: 18/468,732

(22) Filed: Sep. 17, 2023

(65) Prior Publication Data

US 2024/0000401 A1 Jan. 4, 2024

Related U.S. Application Data

(63) Continuation of application No. PCT/CN2022/082556, filed on Mar. 23, 2022.

(30) Foreign Application Priority Data

Mar. 23, 2021 (CN) .......................... 202110330513.9

(51) Int. Cl.
*A61B 6/03* (2006.01)
*G06T 7/00* (2017.01)

(52) U.S. Cl.
CPC ............ *A61B 6/037* (2013.01); *G06T 7/0012* (2013.01); *G06T 2207/10104* (2013.01)

(58) Field of Classification Search
None
See application file for complete search history.

(56) References Cited

U.S. PATENT DOCUMENTS

| | | | |
|---|---|---|---|
| 4,415,807 A | 11/1983 | Friauf et al. | |
| 4,575,888 A | 3/1986 | Ueda et al. | |
| 5,138,165 A | 8/1992 | Petroff | |
| 8,947,585 B2 | 2/2015 | Nagasaka | |
| 2002/0163994 A1 | 11/2002 | Jones | |
| 2005/0242288 A1 | 11/2005 | Wollenweber et al. | |
| 2006/0249682 A1 | 11/2006 | Hogg et al. | |
| 2011/0309256 A1 | 12/2011 | Moriyasu et al. | |
| 2015/0142389 A1 | 5/2015 | Niu et al. | |
| 2015/0289825 A1 | 10/2015 | Lage et al. | |
| 2015/0297168 A1 | 10/2015 | Panin | |

(Continued)

FOREIGN PATENT DOCUMENTS

| CN | 1467488 A | 1/2004 |
|---|---|---|
| CN | 104408783 A | 3/2015 |

(Continued)

OTHER PUBLICATIONS

The Extended European Search Report in European Application No. 22774285.5 mailed on Jul. 1, 2024, 8 pages.

(Continued)

*Primary Examiner* — Samah A Beg
(74) *Attorney, Agent, or Firm* — Metis IP LLC

(57) ABSTRACT

A method for data acquisition in PET may be provided. The method may include obtaining, based on outputs of multiple pairs of detectors of a Positron Emission Tomography (PET) scanner, coincidence events corresponding to multiple LORs. The outputs of the multiple pair of detectors may be acquired during a PET scan on a subject. The method may also include determining, based on a count of coincidence events corresponding to each LOR of at least a portion of the multiple LORs, a detection rate corresponding to the LOR.

20 Claims, 8 Drawing Sheets

500

(56) References Cited

U.S. PATENT DOCUMENTS

| | | | |
|---|---|---|---|
| 2016/0131774 A1 | 5/2016 | Lage et al. | |
| 2017/0357015 A1* | 12/2017 | Li | A61B 6/5211 |
| 2018/0021009 A1* | 1/2018 | Ye | A61B 6/4266 |
| | | | 250/252.1 |
| 2018/0203141 A1* | 7/2018 | Chang | G01T 1/2985 |
| 2019/0015062 A1 | 1/2019 | Liu et al. | |
| 2019/0150877 A1* | 5/2019 | Sun | G01T 1/2985 |
| 2019/0361136 A1* | 11/2019 | Song | G01T 1/249 |
| 2020/0146649 A1 | 5/2020 | Amirrashedi et al. | |
| 2020/0286266 A1 | 9/2020 | Song et al. | |
| 2022/0198656 A1 | 6/2022 | Tang et al. | |
| 2022/0304633 A1 | 9/2022 | Lyu | |
| 2023/0386036 A1* | 11/2023 | Liu | A61B 6/5205 |

FOREIGN PATENT DOCUMENTS

| | | | |
|---|---|---|---|
| CN | 105894525 | A | 8/2016 |
| CN | 106264588 | A | 1/2017 |
| CN | 107320121 | | 11/2017 |
| CN | 108209958 | A | 6/2018 |
| CN | 108523916 | A | 9/2018 |
| CN | 108932740 | A | 12/2018 |
| CN | 109077748 | A | 12/2018 |
| CN | 110368009 | A | 10/2019 |
| CN | 110727011 | A | 1/2020 |
| CN | 110988960 | A | 4/2020 |
| CN | 112022188 | A | 12/2020 |
| CN | 112258506 | A | 1/2021 |
| WO | 2022199630 | A1 | 9/2022 |

OTHER PUBLICATIONS

International Search Report in PCT/CN2022/082556 mailed on Jun. 21, 2022, 5 pages.
Written Opinion in PCT/CN2022/082556 mailed on Jun. 21, 2022, 5 pages.

* cited by examiner

110

500

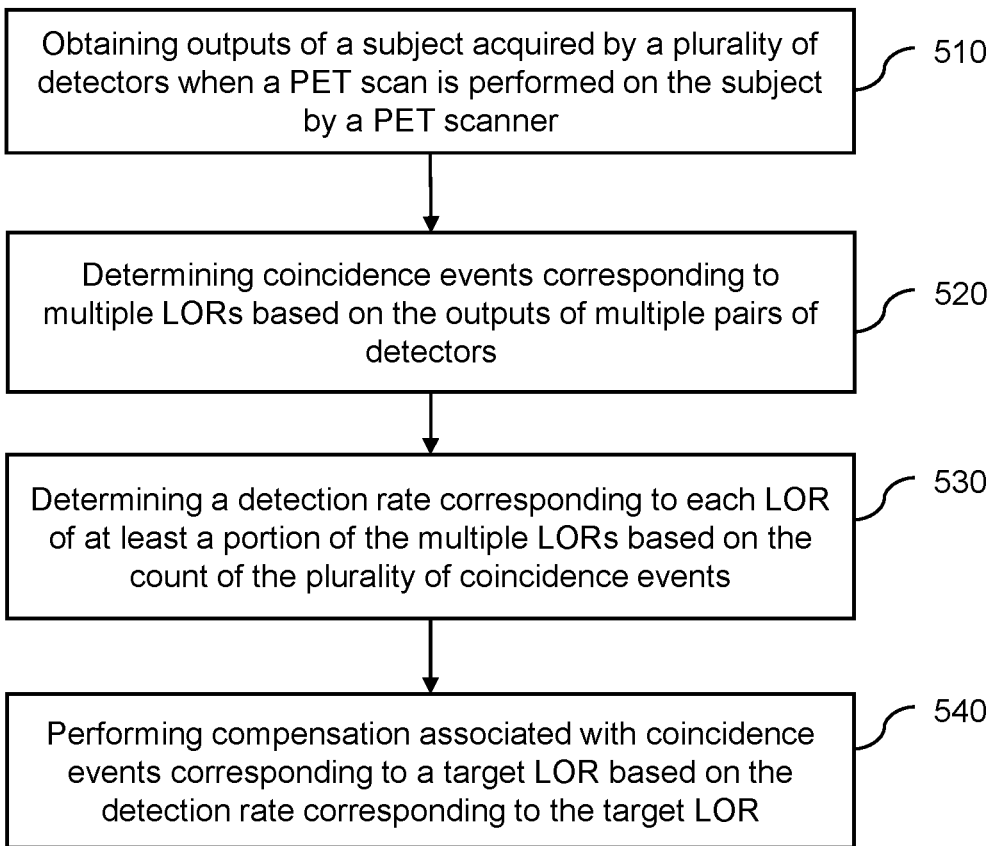

510 — Obtaining outputs of a subject acquired by a plurality of detectors when a PET scan is performed on the subject by a PET scanner 520 — Determining coincidence events corresponding to multiple LORs based on the outputs of multiple pairs of detectors 530 — Determining a detection rate corresponding to each LOR of at least a portion of the multiple LORs based on the count of the plurality of coincidence events 540 — Performing compensation associated with coincidence events corresponding to a target LOR based on the detection rate corresponding to the target LOR

| Coincidence Detection Apparatus | Data Acquisition Apparatus 900 |
|---|---|
| Detector U0M0 Detector U0M1 | Coincidence Event Determination Unit P1 → Detection Rate Determination D1 |
| Detector U0M0 Detector U0M2 | Coincidence Event Determination Unit P2 → Detection Rate Determination D1 |
| Detector U1M0 Detector U3M0 | Coincidence Event Determination Unit P3 → Detection Rate Determination D1 |
| ... | ... |
| Detector U7M0 Detector U7M10 | Coincidence Event Determination Unit Pn → Detection Rate Determination Dn |

FIG. 9

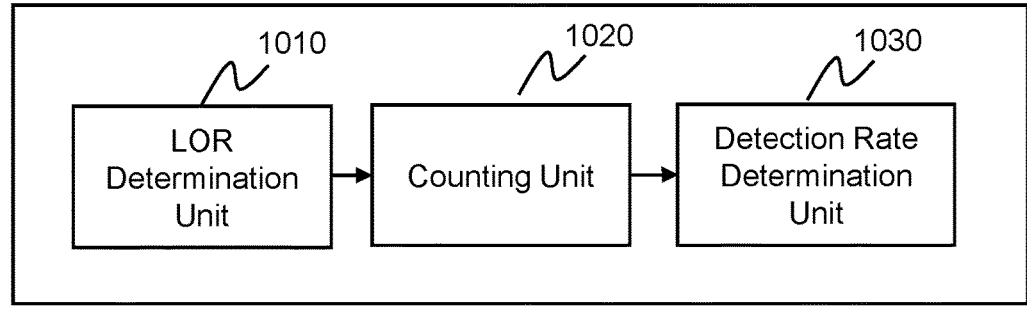

FIG. 10

SYSTEMS, APPARATUSES, AND METHODS FOR DATA ACQUISITION IN PET

CROSS-REFERENCE TO RELATED APPLICATIONS

This application is a Continuation of International Application No. PCT/CN2022/082556 filed on Mar. 23, 2022, which claims priority to Chinese Patent Application No. 202110330513.9, filed on Mar. 23, 2021, the entire contents of which are hereby incorporated by reference.

TECHNICAL FIELD

The present disclosure generally relates to data acquisition and more specifically relates to systems, apparatuses, and methods for data acquisition in PET.

BACKGROUND

A positron emission computed tomography (PET) technology has been widely used in clinical examination and disease diagnosis. With the development of PET technology, the internal structure of a PET detection apparatus becomes more refined, the number of readout channels in the PET detection apparatus increases, and the number of lines of response (LORs) increases sharply. There are some slight differences in physical size, geometric distribution, temperature, etc., between different detectors in the PET detection apparatus, resulting in certain differences in the coincidence detection efficiency of different LORs, thereby decreasing coincidence data quality, and increasing time consumption for processing coincidence data before image reconstruction. Thus, it is desired to provide systems and methods for data acquisition with improved quality and efficiency for PET imaging.

SUMMARY

According to an aspect of the present disclosure, an apparatus for data acquisition for a Positron Emission Tomography (PET) scanner including multiple pairs of detectors may be provided. The apparatus may include a coincidence event determination module configured to obtain, based on outputs of multiple pairs of detectors of a Positron Emission Tomography (PET) scanner, coincidence events corresponding to multiple LORs. The outputs of the detectors may be acquired during a PET scan on a subject. The apparatus may also include a detection rate determination module configured to determine, based on a count of coincidence events corresponding to each LOR of at least a portion of the multiple LORs, a detection rate corresponding to the LOR.

According to an aspect of the present disclosure, a system for data acquisition may be provided. The system may include at least one storage device and at least one processor configured to communicate with the at least one storage devices. The at least one storage device may store a set of instructions. When the at least one processor execute the set of instructions, the at least one processor may be directed to cause the system to perform one or more of the following operations. The system may obtain, based on outputs of multiple pairs of detectors of a Positron Emission Tomography (PET) scanner, coincidence events corresponding to multiple LORs. The outputs of the multiple pair of detectors may be acquired during a PET scan on a subject. The system may also determine, based on a count of coincidence events corresponding to each LOR of at least a portion of the multiple LORs, a detection rate corresponding to the LOR.

According to another aspect of the present disclosure, a method for data acquisition in PET may be provided. The method may include obtaining, based on outputs of multiple pairs of detectors of a Positron Emission Tomography (PET) scanner, coincidence events corresponding to multiple LORs. The outputs of the multiple pair of detectors may be acquired during a PET scan on a subject. The method may also include determining, based on a count of coincidence events corresponding to each LOR of at least a portion of the multiple LORs, a detection rate corresponding to the LOR.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for image data acquisition according to some embodiments of the present disclosure;

FIG. 9 is a schematic diagram illustrating another exemplary data acquisition apparatus according to some embodiments of the present disclosure; and FIG. 10 is a schematic diagram illustrating another exemplary detection rate determination module according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

Figure 1:
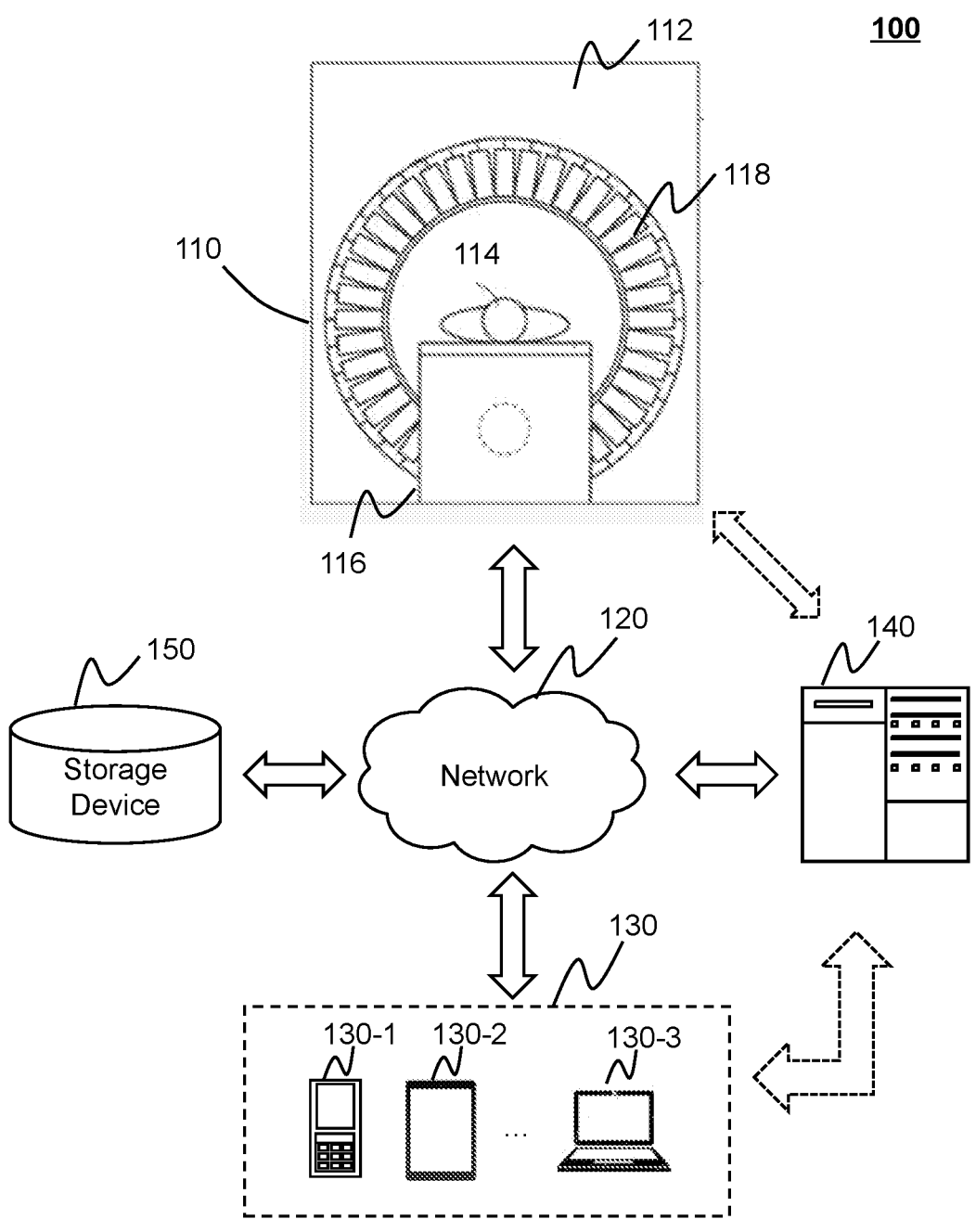
FIG. 1 is a schematic diagram illustrating an exemplary positron emission computed tomography (PET) system according to some embodiments of the present disclosure.

FIG. 1 is a schematic diagram illustrating an exemplary positron emission computed tomography (PET) system according to some embodiments of the present disclosure.

The PET system 100 may include a PET scanner 110, a network 120, a terminal 130, a processing device 140, and a storage device 150. The PET scanner 110 may include a gantry 112, a table 116, a detector apparatus 118, an electronics assembly, and other components (not shown). In some embodiments, when the PET scanner 110 performs a PET scan, a subject 114 injected with a substance labeled with a tracer for the imaging purposes may be placed on the table 116. The subject 114 may be biological or non-biological. Merely by way of example, the subject 114 may include a patient, a man-made object, etc., or a portion thereof. The gantry 112 may support one or more parts of the PET scanner 110, for example, the detector apparatus 118, an electronics assembly, and/or other components. The detector apparatus 118 may detect radiation photons (e.g., y photons) emitted from an object being examined. The detector apparatus 118 may include a plurality of detectors. The electronics assembly may include a data acquisition apparatus and a data transmitting link. The data acquisition apparatus may be configured to determine coincident events by processing outputs (e.g., electrical signals (e.g., pulses) of the detector apparatus 118. More descriptions for the data acquisition apparatus may be found elsewhere in the present disclosure (e.g., FIGS. 6-10).

The network 120 may facilitate the exchange of information and/or data. In some embodiments, one or more components in the PET system 100 (e.g., the PET scanner 110, the terminal 130, the processing device 140, or the storage device 150) may send information and/or data to other component(s) in the PET system 100 via the network 120.

The terminal 130 may include a mobile device 130-1, a tablet computer 130-2, a laptop computer 130-3, or the like, or any combination thereof. In some embodiments, the terminal 130 may receive information and/or instructions inputted by a user, and transmit the received information and/or instructions to the PET scanner 110 or to the processing device 140 via the network 120.

The processing device 140 may process data and/or information obtained from the PET scanner 110, the terminal 130, or the storage device 150. For example, the processing device 140 may cause the data acquisition apparatus to obtain and/or output coincidence events of a subject as described elsewhere in the present disclosure (e.g., FIGS. 5-10). As another example, the processing device 140 may cause the data acquisition apparatus to determine detection rates of multiple LORs and perform compensation based on the detection rates as described elsewhere in the present disclosure (e.g., FIGS. 5-10). In some embodiments, the processing device 140 may be implemented on a computing device 300 having one or more components illustrated in FIG. 3 in the present disclosure.

The storage device 150 may store data and/or instructions. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure.

Figure 2A:
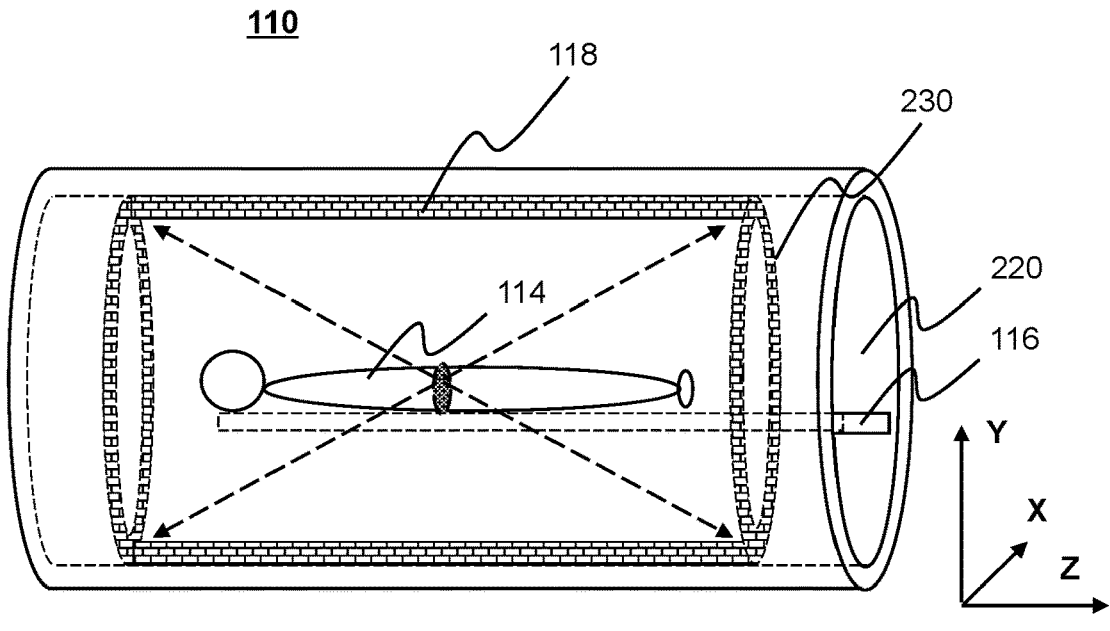
FIG. 2A and FIG. 2B are schematic diagrams illustrating a PET scanner according to some embodiments of the present disclosure.
Figure 2B:
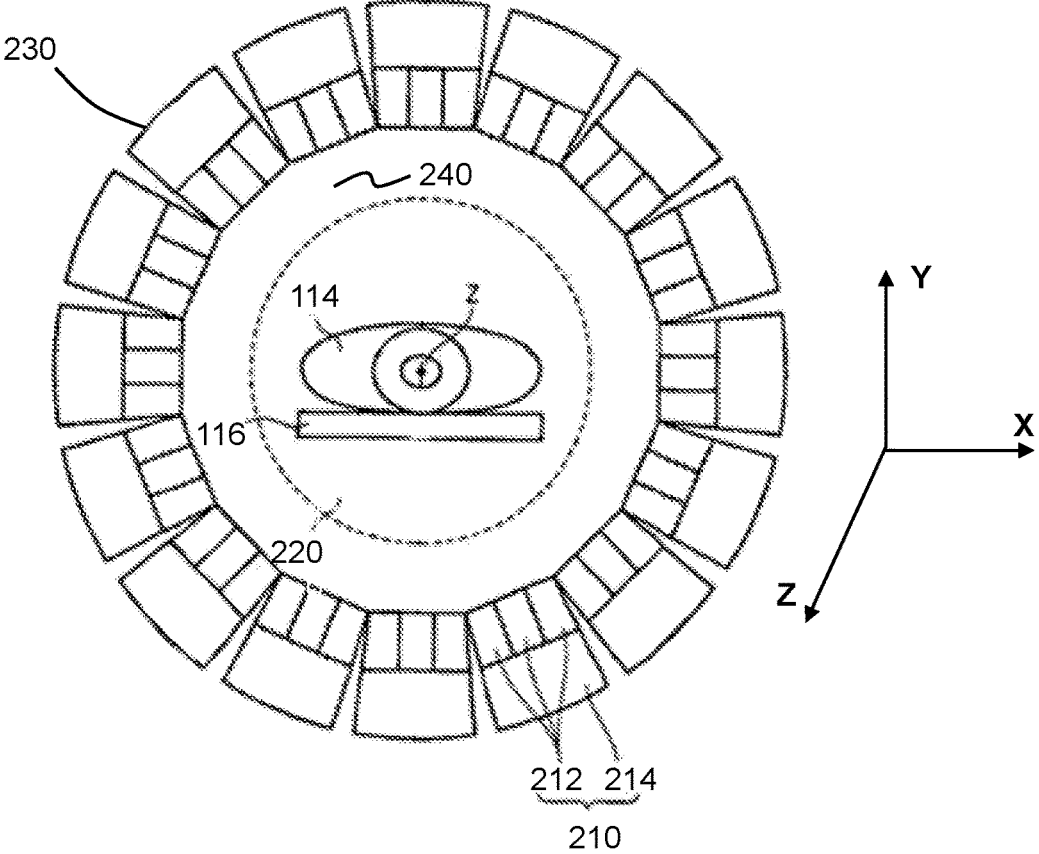

FIG. 2A is a schematic diagram illustrating the PET scanner 110 according to some embodiments of the present disclosure. FIG. 2B is a cross-section of the PET scanner 110 according to some embodiments of the present disclosure. As shown in FIGS. 2A and 2B, the detector apparatus 118 may include a plurality of detector rings arranged along a Z-axial direction (also referred to as a direction of a Z-axis). A detector ring may also be referred to as a detector unit. A detector ring (e.g., a detector ring 230) may include a plurality of detectors (e.g., a detector 210) arranged along the circumference of the detector ring 230 in a plane perpendicular to the Z-axial direction. The plane perpendicular to the Z-axial direction may be defined by an X-axis and a Y-axis. A region encircled by the detector rings may be a detection region 240. The detection region 240 may accommodate the subject 114 to be scanned. The axial field of view (AFOV) of the detector apparatus 118 may be in a range from 0.75 meters to 2 meters. In some embodiments, different lengths of the AFOV may correspond to different numbers of LORs.

In some embodiments, a detector may include a scintillator 212 and a photodetector 214. In some embodiments, the scintillator 212 may include an array of scintillation crystals. The two photons (a pair of photons) generated by an annihilation reaction that occurs inside the subject 14 may be detected by two detectors (also referred to as a pair of detectors) or scintillation crystals in the pair of detectors. Each of the two photons generated by the annihilation reaction may strike the scintillator 212 to produce a burst of fluorescent light. The fluorescence light may be converted to an electrical signal (e.g., an electrical pulse) by the photodetector 214. The electrical signal (i.e., outputs of the pair of detectors) may be transmitted to other components of the PET scanner, such as a data acquisition apparatus.

In some embodiments, the plurality of detector rings may be numbered with first serial numbers along the Z-axial direction. For example, the plurality of detector rings may be numbered with U0, U1, U2, . . . , UQ in sequence along the Z-axial direction. A first serial number of a detector ring may indicate a position of the detector ring in the Z-axial direction. Detectors in the same detector ring may have the same first serial number. In some embodiments, detectors in each of the plurality of detector rings may be numbered with second serial numbers along the circumferential direction of the detector ring. For example, the detectors may be numbered with M0, M1, M2, . . . , MN in sequence along the circumferential direction of a detector ring. A second serial number of a detector in a detector ring may indicate a position of the detector in the detector ring in the circumferential direction (i.e., a position on the X-Y plane). A position of a detector in a space may be defined by a first serial number that indicates a Z-axial position and a second serial number that indicates an X-axial and Y axial position.

Figure 3:
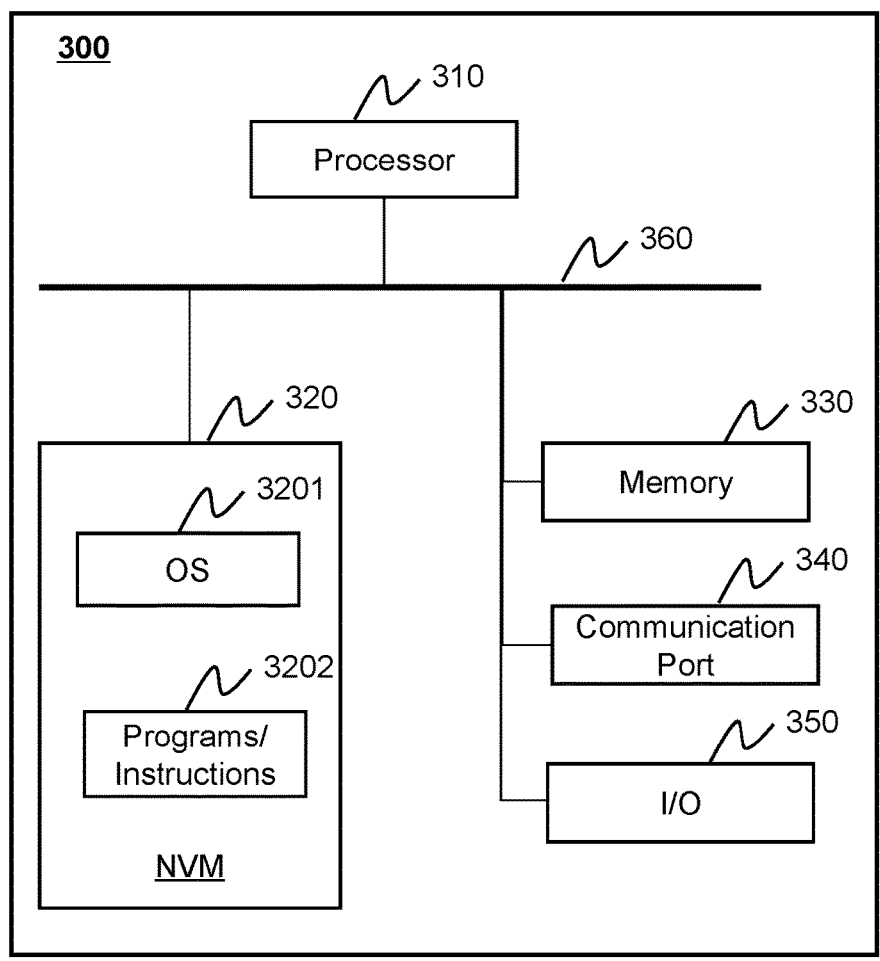
FIG. 3 is a schematic diagram illustrating exemplary hardware and/or software components of a computing device on which a processing device may be implemented according to some embodiments of the present disclosure.

FIG. 3 is a schematic diagram illustrating exemplary hardware and/or software components of a computing device on which the processing device 140 may be implemented according to some embodiments of the present disclosure. As illustrated in FIG. 3, the computing device 300 may include a processor 310, nonvolatile memory (NVM) 320, memory 330, a communication port 340, and an input/output (I/O) 350 connected via a bus 360. The processor 310 may execute computer instructions (program code) and perform functions of the processing device 140 in accordance with the present disclosure described herein. NVM 320 may store an operating system (OS) 3201 and one or more programs and/or instructions 3202 to be executed by the processor 310. The methods and/or processes of the present disclosure may be implemented as the program and/or instructions. The memory 330 may support operations of the OS 3201 and the one or more programs and/or instructions 3202. The communication port 340 may be connected to a network (e.g., the network 120) to facilitate data communications. In some embodiments, the I/O 350 may enable user interaction with the processing device 140 (i.e., the computing device 300).

Figure 4:
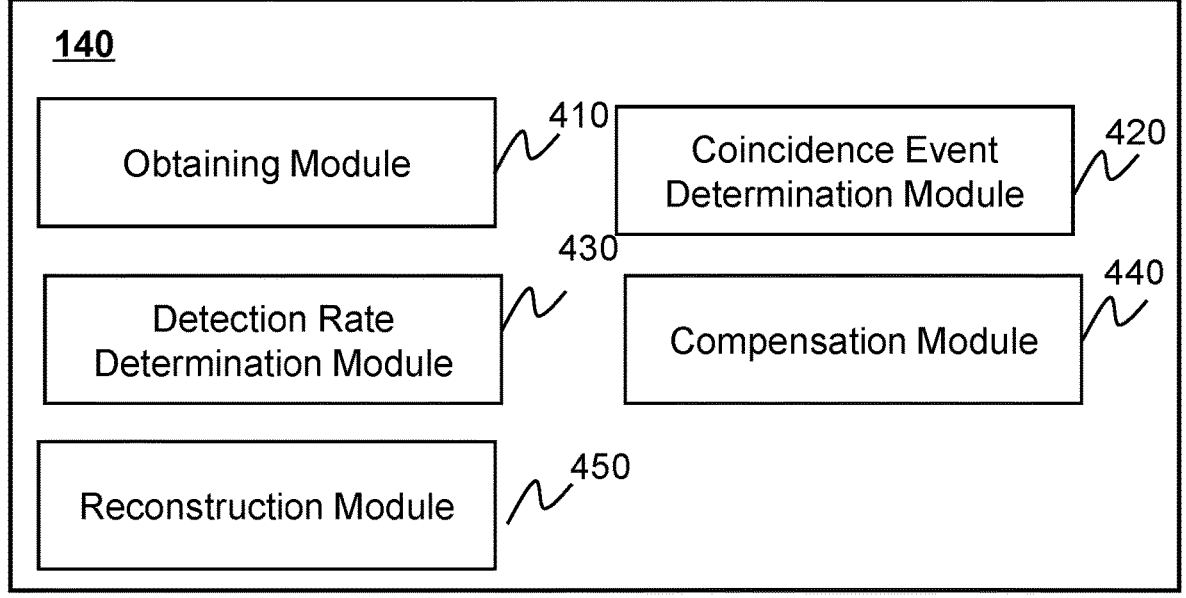
FIG. 4 is a block diagram illustrating an exemplary processing device according to some embodiments of the present disclosure.

FIG. 4 is a block diagram illustrating an exemplary processing device 140 according to some embodiments of the present disclosure. The processing device 140 may be implemented on the computing device 300 as described in FIG. 3. The processing device 140 may include an obtaining module 410, a coincidence event determination module 420, a detection rate determination module 430, a compensation module 440, and a reconstruction module 450. In some embodiments, the processing device 140 may be an apparatus for data acquisition for a PET scanner. It should be noted that the descriptions of the obtaining module 410, the coincidence event determination module 420, the detection rate determination module 430, the compensation module 440, and the reconstruction module 450 that are integrated into the same processing device in FIG. 4 are merely provided for the purposes of illustration, and not intended to limit the scope of the present disclosure. In some embodiments, at least two of the obtaining module 410, the coincidence event determination module 420, the detection rate determination module 430, the compensation module 440, and the reconstruction module 450 may be implemented on different processing devices (e.g., computing devices, processors, circuit boards).

The obtaining module 410 may obtain outputs of a plurality of detectors when a PET scanner performs a PET scan on a subject. Each two (also referred to as a pair of detectors) of the plurality of detectors may be on a LOR of the PET scanner. More descriptions for the obtaining of the outputs of the plurality of detectors may be found elsewhere in the present disclosure (e.g., FIG. 5 and the descriptions thereof).

The coincidence event determination module 420 may determine a plurality of coincidence events corresponding to each LOR of at least a portion of LORs of the PET scanner. The coincidence event determination module 420 may also be referred to as a coincidence detection apparatus. More descriptions for the coincidence event determination module may be found elsewhere in the present disclosure (e.g., FIGS. 5 and 6, and the descriptions thereof).

The detection rate determination module 430 may determine a detection rate corresponding to each of at least a portion of the multiple LORs based on a count of the coincidence events corresponding to the each of at least a portion of the multiple LORs. More descriptions for the detection rate determination module may be found elsewhere in the present disclosure (e.g., FIGS. 5-10, and the descriptions thereof).

The compensation module 440 may perform compensation associated with coincidence events corresponding to a target LOR based on the detection rate corresponding to the target LOR. More descriptions for the detection rate determination module may be found elsewhere in the present disclosure (e.g., FIGS. 5 and 6, and the descriptions thereof).

The image reconstruction module 450 may be configured to determine a PET image and/or other parameters (e.g., SUVs) based on the coincidence events. The image reconstruction module 450 may obtain compensated coincidence events corresponding to the one or more target LORs from the compensation module 440. In some embodiments, the image reconstruction module 450 may obtain coincidence events corresponding to the remaining LORs of the LORs excepting the one or more target LORs from the coincidence event determination module 420. More descriptions for the image reconstruction module may be found elsewhere in the present disclosure (e.g., FIGS. 5 and 8, and the descriptions thereof). In some embodiments, the image reconstruction module 450 may obtain coincidence events corresponding to the remaining LORs of the LORs excepting the one or more target LORs from the compensation module 440.

FIG. 5 is a flowchart illustrating an exemplary process 500 for image data acquisition according to some embodiments of the present disclosure.

In 510, outputs of a plurality of detectors when a PET scanner performs a PET scan on a subject may be obtained. Operation 510 may be performed by the processing device 140 (e.g., the obtaining module 410 or the coincidence event determination module 420) or a data acquisition apparatus (e.g., the coincidence event determination module 610 of the data acquisition apparatus 600, or the coincidence event determination module 710 of the data acquisition apparatus 700, etc.).

The subject may a patient, a man-made object, etc. For example, the subject may include a specific portion, organ, and/or tissue of the patient.

The outputs may be generated after a tracer is injected into the subject when the PET scan is performed. For example, after a tracer is injected into the subject, annihilation reactions may occur. An annihilation reaction may simultaneously generate two photons (e.g., 511-kiloelectron volt (keV) gamma photons) traveling in opposite directions along a line. The two photons may be detected by two detectors (also referred to as a pair of detectors) on the line. The two detectors may generate electrical signals (i.e., outputs) including information (e.g., time information, energy information, position information of the pair of detectors) associated with the detected photons after detecting the two photons. As used herein, the time when a photon is detected by a detector may be equivalent or approximate to a time when the output of the detector is generated.

The plurality of detectors may transmit the outputs in real-time or periodically. For example, in response to detecting a photon and generating an electrical signal, the detector may transmit the electrical signal to a data acquisition apparatus or a coincidence event determination module. As another example, the detector may transmit electrical signals to a data acquisition apparatus or a coincidence event determination module every time period (also referred to as a first time period, e.g., 1 millisecond, 2 milliseconds, etc.).

In 520, coincidence events corresponding to multiple LORs may be determined based on the outputs of the multiple pairs of detectors. Operation 520 may be performed by the processing device 140 (e.g., the coincidence event determination module 420) or a data acquisition apparatus (e.g., the coincidence event determination module 610 of the data acquisition apparatus 600, or the coincidence event determination module 710 of the data acquisition apparatus 700, etc.).

As used herein, a coincidence event corresponding to a LOR refers to a pair of photons associated with the coincidence event traveling along a line and being detected by a pair of detectors connected by the line (i.e., the LOR) within a coincidence window range. Each LOR of the multiple LORs may be generated after a pair of photons travel along a line and are detected by a pair of detectors on the line within a coincidence window range. In other words, an annihilation position of an annihilation reaction for generating the single radiation events associated with (or composed of) the coincidence event corresponding to a LOR is located on the LOR. The coincidence event corresponding to a LOR may also be referred to as a coincidence event on the LOR. Coincidence events corresponding to LORs with the same identity (i.e., connecting the same pair of detectors or scintillation crystals) may also be referred to as coincidence events corresponding to a LOR.

A plurality of coincidence events corresponding to a LOR may be determined based on the outputs of a pair of detectors connected by the LOR. In some embodiments, the plurality of coincidence events corresponding to the LOR may be determined based on the outputs of the LOR in a time period. As used herein, the time period when a coincidence event is generated based on the outputs of a pair of detectors may be equivalent to or approximate to the time period when the outputs of the pair of detectors are generated. For example, the plurality of coincidence events corresponding to the LOR determined based on the outputs of the pair of detectors generated in the first time period may refer to that the plurality of coincidence events are generated in the first time period. As another example, the plurality of coincidence events corresponding to the LOR determined based on the outputs of the pair of detectors generated in several consecutive first time periods may refer to that the plurality of coincidence events are generated in the several consecutive first time periods.

In some embodiments, the time period (also referred to as a second time period) may be the first time period. In some embodiments, the time period may be several first time periods. In some embodiments, the time period may be a portion or a segment of the total time period of the PET scan. The length of the time period may be 1 second, 2 seconds, 4 seconds, 10 seconds, 1 minute, etc. The length of the time period may be a default setting of the system or set by an operator. In some embodiments, the time period may be the total time period of the PET scan.

For the plurality of detectors, any two of the plurality of detectors may be defined as a pair of detectors on a LOR. The plurality of detectors may be divided into multiple pairs of detectors each of which may correspond to one of the multiple LORs. Coincidence events corresponding to each of the multiple LORs of the PET scanner may be determined based on outputs of one pair of the multiple pairs of detectors. A coincidence event may be a truth coincidence event, a random coincidence event, or a scatter coincidence event. A pair of photons in the truth coincidence event may be generated by the same annihilation reaction and emitted from the same annihilation position; a pair of photons in the random coincidence event or the scatter coincidence event may be generated by different annihilation reactions and emitted from different annihilation positions.

For a pair of detectors on a LOR, outputs generated by the pair of detectors may be used to determine coincidence events corresponding to the LOR. For example, the outputs may include time information associated with multiple photons detected by the pair of detectors. The time information associated with any two photons among the multiple photons detected by the pair of detectors may be compared to determine whether the two photons correspond to a coincidence event. For example, a time difference between the times when the two photons are detected by the pair of detectors may be determined based on the time information. If the time difference is within a coincidence window range, the two photons may correspond to a coincidence event.

Figure 6:
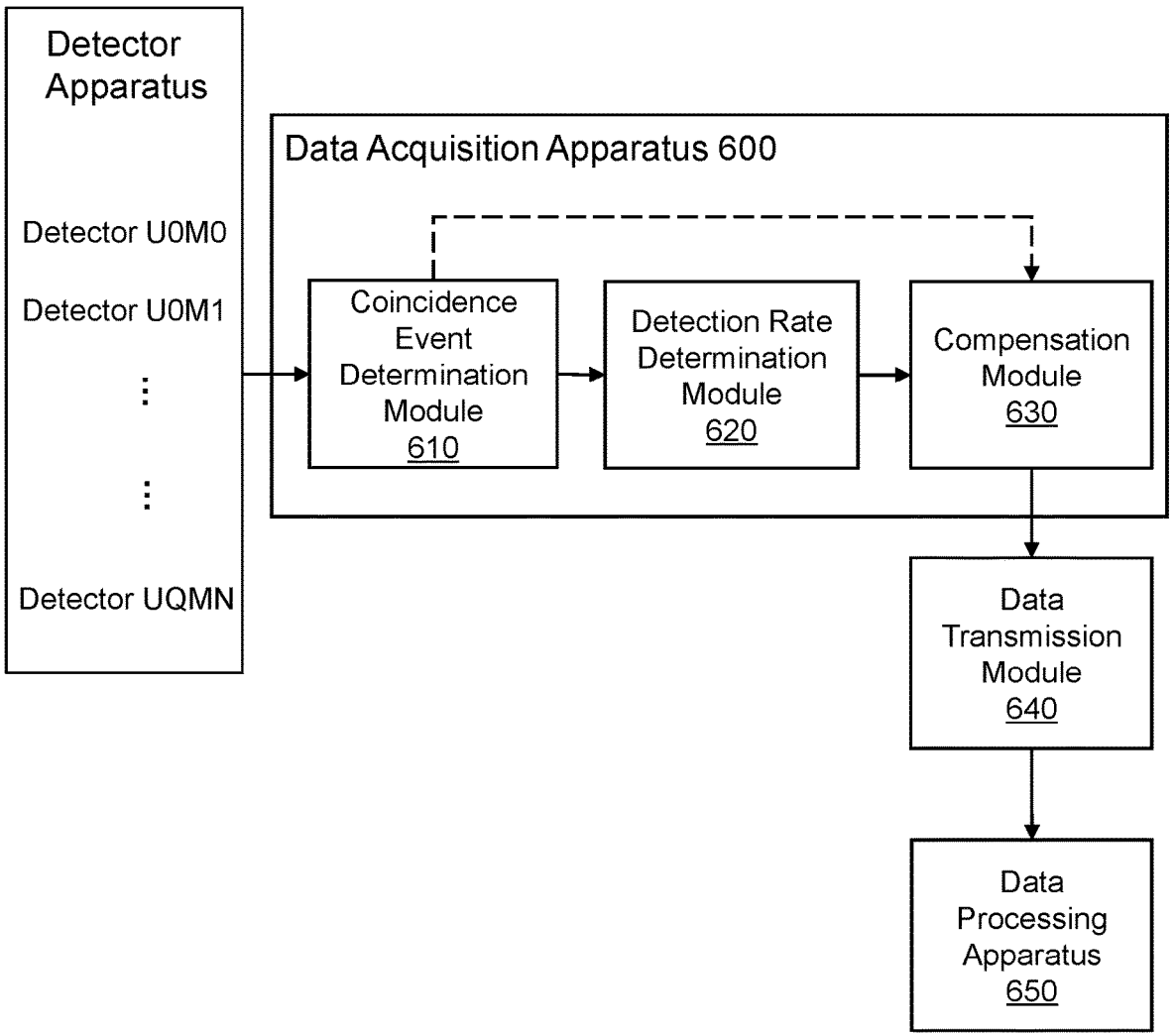
FIG. 6 is a schematic diagram illustrating an exemplary data acquisition apparatus according to some embodiments of the present disclosure.

More descriptions for coincidence detection may be found elsewhere in the present disclosure (e.g., FIG. 6 and the descriptions thereof).

In 530, a detection rate corresponding to each LOR of at least a portion of the multiple LORs may be determined based on the count of the plurality of coincidence events corresponding to the LOR. Operation 530 may be performed by the processing device 140 (e.g., the detection rate determination module 430) or a data acquisition apparatus (e.g., the detection rate determination module 620 of the data acquisition apparatus 600, or the detection rate determination module 720 of the data acquisition apparatus 700, etc.).

In some embodiments, a detection rate corresponding to each of at least a portion of the multiple LORs in a time period may be determined based on a count of a plurality of coincidence events generated in a time period (e.g., 1 second, 2 seconds, 10 seconds, 1 minute, 10 minutes, the total time period of the PET scan, etc.). The time period may also be referred to as the second time period as described in operation 520.

As used herein, a detection rate corresponding to a LOR refers to a count (number) of coincidence events per unit time determined based on outputs acquired by a pair of detectors on the LOR. The detection rate corresponding to a LOR may be a ratio of the count of coincidence events corresponding to the LOR and the length of the time period. More descriptions for the determination of the detection rate may be found elsewhere in the present disclosure (e.g., FIGS. 6-10 and the descriptions thereof).

In some embodiments, a detection rate corresponding to each of at least a portion of the multiple LORs in every time period may be determined based on the count of a plurality of coincidence events generated in every time period. For example, the PET scanner may include a data acquisition apparatus (e.g., the data acquisition apparatus 600, or the data acquisition apparatus 700, the data acquisition apparatus 800, or the data acquisition apparatus 900, etc.). The data acquisition apparatus may include a coincidence detection module and a detection rate determination module. For every time period (e.g., 1 second, 2 seconds, 10 seconds, etc.) during the PET scan of the subject, the detection rate determination module may determine the count of coincidence events corresponding to each LOR determined in every time period and determine the detection rate of each LOR in every time period.

In some embodiments, the PET scanner may include a data processing apparatus (e.g., the data processing apparatus 650, the data processing apparatus 750, or data processing apparatus 850, etc.). The data processing apparatus may obtain coincidence events outputted by a data acquisition apparatus and determine the detection rate based on the coincidence events corresponding to each LOR in every time period or the total time period of the PET scan. More descriptions for the determination of the detection rate may be found elsewhere in the present disclosure (e.g., FIG. 6 and the descriptions thereof).

In 540, a compensation associated with coincidence events corresponding to a target LOR may be performed based on the detection rate corresponding to the target LOR. Operation 540 may be performed by the processing device 140 (e.g., the compensation module 440) or a data acquisition apparatus (e.g., the compensation module 630 of the data acquisition apparatus 600, or the compensation module 730 of the data acquisition apparatus 700, etc.).

In some embodiments, the target LOR may be determined based on the detection rate corresponding to the target LOR and a reference detection rate. In some embodiments, the target LOR may be a LOR whose detection rate is smaller than the reference detection rate. In some embodiments, the target LOR may be a LOR whose detection rate is smaller than the reference detection rate and exceeds a detection rate threshold. The detection rate threshold may be a default setting of the system 100. For example, the detection rate threshold may be determined based on the reference detection rate. As a further example, a ratio of the detection rate threshold and the reference detection rate may be 0.7, 0.6, 0.5, 0.4, etc.

In some embodiments, the reference detection rate may be obtained by performing a PET scan on a reference subject. The reference subject may be a standard phantom. The standard phantom may include a tubular or cylindrical structure. The standard phantom may be located at the center of the detection region of the PET scanner. In some embodiments, the PET scan on the reference subject may be performed before the PET scan on the subject. In some embodiments, the reference detection rate may be updated periodically or randomly. The PET scan may be performed on the reference subject periodically or randomly to update the reference detection rate. More descriptions for the determination of the reference detection rate may be found elsewhere in the present disclosure (e.g., FIGS. 6 and 7 and the descriptions thereof).

In some embodiments, the compensation associated with the coincidence events corresponding to the target LOR may be performed by duplicating a portion of the coincidence events corresponding to the target LOR based on the detection rate corresponding to the detection rate. More descriptions for the compensation may be found elsewhere in the present disclosure (e.g., FIGS. 6 and 7 and the descriptions thereof).

In some embodiments, the compensation associated with the coincidence events corresponding to the target LOR may be performed by the data acquisition apparatus (e.g., the compensation module 630 of the data acquisition apparatus 600, or the compensation module 730 of the data acquisition apparatus 700, etc.). In some embodiments, the compensation associated with the coincidence events corresponding to the target LOR may be performed by the data processing apparatus (e.g., the compensation module 851 of the data processing apparatus 850, etc.).

In some embodiments, one or more PET images may be reconstructed based on the compensation coincidence events corresponding to one or more target LORs and the coincidence events corresponding to one or more remaining LORs among the multiple LORs excepting the target LORs.

According to some embodiments of the present disclosure, the data acquisition apparatus may determine the detection rates of the multiple LORs in every time period (e.g., 1 second, 2 seconds, 1 minute, etc.) and may perform compensation associated with coincidence events corresponding to LORs generated in a time period whose detection rates are abnormal in the time period. Determining the detection rates corresponding to the LORs in every time period may reduce the amount of data that needs to process for determining the detection rates and may not generate delays for data processing (e.g., compensation, detection rate determination in next time periods), thereby improving the speed of data processing. The compensation associated with coincidence events corresponding to LORs performed in every time period may also reduce the amount of data that needs to process and may not generate delays for data processing (e.g., compensation in next time periods), and also increase data (e.g., the coincidence events) quality in the time period. Accordingly, the data acquisition apparatus may effectively and accurately determine detection rates and perform compensation, thereby improving the efficiency and quality of data for image reconstruction or other processing.

FIG. 6 is a schematic diagram illustrating an exemplary data acquisition apparatus according to some embodiments of the present disclosure. At least a portion of process 500 may be performed by the data acquisition apparatus 600 as shown in FIG. 6. As shown in FIG. 6, the data acquisition apparatus may include a coincidence event determination module 610, a detection rate determination module 620, and a compensation module 630.

The coincidence event determination module 610 may be configured to detect coincidence events based on outputs of a plurality of detectors in a detector apparatus. The detector apparatus may be the same as or similar to the detector apparatus 118 as described in FIG. 2A. For example, the detector apparatus may include a plurality of detectors configured to detect photons emitted from a subject when the subject involves a PET scan and output data (i.e., outputs of the detectors) including information of the detected photons (i.e., information of single radiation events). Each of the plurality of detectors in the detector apparatus may be numbered with a first serial number and a second serial number for identification of the position of the detector. The output of a detector may include information of a photon (e.g., time information, position information of the detector) that is detected by the detector (also referred to as information of a single radiation event). Each of the plurality of detectors in the detector apparatus may transmit the output to the coincidence event determination module 620 in real-time or periodically. For example, a detector may be configured to transmit the output in response to the generation of the output or every time period (also referred to as a first time period, e.g., 1 millisecond, 2 milliseconds, 3 milliseconds, etc.) during the PET scan.

In some embodiments, for a pair of detectors among the plurality of detectors, the coincidence event determination module 610 may be configured to determine coincidence events corresponding to a LOR connecting the pair of detectors based on the photon information of photons (e.g., time information) detected by the pair of detectors. The coincidence event determination module 610 may obtain the photon information of every two photons (e.g., time information) that are detected by the pair of detectors. The coincidence event determination module 610 may be configured to determine a time difference between the times when the two photons are detected by the pair of detectors, respectively. The coincidence event determination module 610 may be configured to determine a coincidence event by determining whether the time difference between the times when the two photons are detected by the pair of detectors is located within a coincidence window range (i.e., a time range). If the time difference is located within the coincidence window range (i.e., a time range), the coincidence event determination module 610 may determine the two photons that are detected by the pair of detectors correspond to a coincidence event. The coincidence event may include information of the photons (or single radiation events) that are detected by the pair of detectors, e.g., the time information, the position information of the pair of detectors, energy information of the photons, etc.

In some embodiments, the coincidence event determination module 610 may be configured to determine coincidence events in every time period (also referred to as a first time period) during the PET scan for each of the multiple LORs of the PET scanner. For example, during a total time period (e.g., 10 minutes, 20 minutes, 30 minutes, 60 minutes, etc.) of the PET scan of the subject, the coincidence event determination module 610 may obtain photon information of multiple photons (e.g., time information) that are detected by the plurality of detectors within every time period (e.g., 1 millisecond, 2 milliseconds, 3 milliseconds, etc.). The coincidence event determination module 610 may determine coincidence events corresponding to each LOR of at least a portion of the LORs within the time period based on the photon information of the multiple photons. If two photons (also referred to as a pair of photons) among the multiple photons correspond to a coincidence event, the coincidence event determination module 610 may transmit the coincidence event and/or information associated with the coincidence event (e.g., a signal indicating that the coincidence event is detected) to the detection rate determination module 620 in real-time or periodically. The information associated with the coincidence event may include position information of a pair of detectors that detects single radiation events corresponding to the coincidence event, the information or a signal indicating that the coincidence event is detected (e.g., the information indicating that the coincidence event is detected may include a value "1"), an identity of the LOR where the coincidence event is on, etc. In some embodiments, the coincidence event determination module 610 may transmit coincidence events and/or information associated with the coincidence events to the detection rate determination module 620 every time period (e.g., the first time period) or transmit coincidence events to the detection rate determination module 620 in response to the detection of the coincidence event. In some embodiments, the coincidence event determination module 610 may transmit the coincidence events and/or information associated with the coincidence events corresponding to at least a portion the LORs to the compensation module 630 in real-time or periodically.

In some embodiments, the detection rate determination module 620 may be configured to determine a detection rate corresponding to each LOR of at least a portion of the LORs. In some embodiments, the detection rate determination module 620 may be configured to determine a detection rate corresponding to a LOR within every time period (also referred to as a second time period). The length of the second time period may be 1 second, 2 seconds, 10 seconds, 20 seconds, 30 seconds, 40 seconds, 50 seconds, 1 minute, 2 minutes, 4 minutes, 6 minutes, 10 minutes, etc. The length of the second time period may exceed the length of the first time period.

In some embodiments, for a current time period in the total time period of a PET scan, the detection rate determination module 620 may determine a detection rate corresponding to a LOR in the current time period based on a count of coincidence events corresponding to the LOR that are determined based on outputs of a pair of detectors on the LOR generated in the current time period. The detection rate determination module 620 may determine the detection rate corresponding to the LOR based on the count of coincidence events corresponding to the LOR and the length of the time period. For example, the detection rate corresponding to the LOR may be a ratio of the count of coincidence events corresponding to the LOR and the length of the time period.

In some embodiments, the detection rate determination module 620 may determine the count of coincidence events corresponding to the LOR based on information associated with the coincidence events (e.g., position information of a pair of detectors on the LOR). For example, the detection rate determination module 620 may obtain information associated with coincidence events corresponding to the LORs of the PET scanner. The detection rate determination module 620 may determine, based on the position information of the pair of detectors included in each of the coincidence events, identities of the LORs and determine the count of the coincidence events corresponding to the LOR based on coincidence events corresponding to LORs with the same identity of the LOR. The detection rate determination module 620 may determine the identity of a LOR based on the position information of a pair of detectors on the LOR. For example, the position information of a pair of detectors may be denoted by the serial numbers of each of the pairs of detectors. More descriptions for the detection rate determination module 620 may be found elsewhere in the present disclosure (e.g., FIG. 10 and the descriptions thereof). In some embodiments, the detection rate determination module 620 may output the detection rate corresponding to each LOR and/or coincidence events corresponding to each LOR to the compensation module 630 periodically. For example, in response to the determination of the detection rate corresponding to each LOR (i.e., every second time period), the detection rate determination module 620 may output the detection rate to the compensation module 630.

The compensation module 630 may determine one or more target LORs whose detection rates are abnormal and perform a compensation operation associated with the coincidence events corresponding to each of the one or more target LORs to obtain compensated coincidence events. In some embodiments, the compensation module 630 may transmit the compensated coincidence events corresponding to the one or more target LORs to the data transmission module 640 and the coincidence event determination module 610 may transmit coincidence events corresponding to the remaining LORs among the LORs excepting the target LORs to the data transmission module 640. The data transmission module 630 may transmit the coincidence events and compensated coincidence events to a data processing apparatus 650 (e.g., a processing device for image reconstruction) along a data transmitting link for further processing. For example, the data processing apparatus 650 may reconstruct a PET image based on the compensated coincidence events corresponding to the one or more target LORs and the coincidence events corresponding to the remaining LORs. The data transmitting link may include one or more devices for transmitting the coincidence events. For example, the data transmitting link may include a data acquisition hardware (e.g., an acquisition (ACQ) board), a data acquisition software (e.g., a Redis desktop manager (RDM)), and a data storage device (e.g., a Redis desktop manager (SSD)).

In some embodiments, the coincidence event determination module 610 may transmit the coincidence events corresponding to each LOR to the compensation module 630 directly and the detection rate determination module 620 may transmit the detection rate corresponding to each LOR to the compensation module 630. The compensation module 630 may transmit the compensated coincidence events corresponding to the one or more target LORs and the coincidence events corresponding to the remaining LORs among the LORs excepting the target LORs to the data transmission module 640.

In some embodiments, the coincidence event determination module 610 may transmit the coincidence events corresponding to each LOR to the detection rate determination module 620. The detection rate determination module 620 may transmit the coincidence events and the detection rate corresponding to each LOR to the compensation module 630 directly. The compensation module 630 may transmit the compensated coincidence events corresponding to the one or more target LORs and the coincidence events corresponding to the remaining LORs among the LORs excepting the target LORs to the data transmission module 640.

In some embodiments, the compensation module 630 may determine the one or more target LORs based on reference detection rates of the multiple LORs. Each of the multiple LORs may correspond to a reference detection rate. In some embodiments, the compensation module 630 may determine a target LOR by comparing a detection rate corresponding to a LOR with the reference detection rate corresponding to the LOR. For example, if the detection rate corresponding to a LOR is less than the detection reference rate, the compensation module 630 may designate the LOR as a target LOR. As another example, if a difference between the detection rate corresponding to a LOR and the reference detection rate of the LOR exceeds a threshold, the compensation module 630 may designate the LOR as a target LOR.

The reference detection rates of the multiple LORs may be obtained by performing a PET scan on a reference subject. The reference subject may be a standard phantom. The standard phantom may include a tubular structure or a cylindrical structure. The standard phantom may be hollow and a radiation source may be injected and located inside the standard phantom. The standard phantom may be located at the center of the detection region of the PET scanner. The reference detection rates of the multiple LORs may be determined based on the count of reference coincidence events corresponding to each of the multiple LORs. The reference coincidence events corresponding to a LOR may be determined based on outputs of a pair of detectors on the LOR when the PET scan is performed on the reference subject. Further, each of multiple candidate detection rates corresponding to one of the LORs may be determined based on a count of reference coincidence events corresponding to each of the LORs and the length of a time period during which the reference coincidence events are detected. The reference detection rate corresponding to each of the LORs may be determined based on the candidate detection rates. In some embodiments, the reference detection rates corresponding to the LORs may be the same. The reference detection rates corresponding to the LORs may be equal to an average, a median, a maximum, or a minimum of the candidate detection rates. In some embodiments, a reference detection rate corresponding to a LOR may be the candidate detection rate corresponding to the LOR.

In some embodiments, the compensation module 630 may perform a compensation associated with the coincidence events corresponding to a target LOR based on the detection rate of the target LOR and the reference detection rate of the target LOR. In some embodiments, the compensation module 630 may determine a compensation coefficient corresponding to the target LOR based on the reference detection rate and the reference rate of the target LOR. The compensation module 630 may perform the compensation based on the compensation coefficient corresponding to the target LOR. In some embodiments, the compensation coefficient corresponding to the target LOR may be a ratio of the reference detection rate of the target LOR and the detection rate of the LOR.

In some embodiments, the compensation module 630 may perform compensation on the coincidence events corresponding to a target LOR to obtain compensated coincidence events based on the compensation coefficient. In some embodiments, the compensation module 630 may duplicate a portion of the coincidence events corresponding to the target LOR based on the compensation coefficient corresponding to the target LOR. The proportion of the portion of the coincidence events that need to be duplicated in the coincidence events may be a difference between the compensation coefficient and value 1. As a further example, if the compensation coefficient is 1.5, the data processing module 630 may duplicate half of the coincidence events. The compensated coincidence events may be generated by combining the duplicated portion of the coincidence events and the coincidence events.

Figure 7:
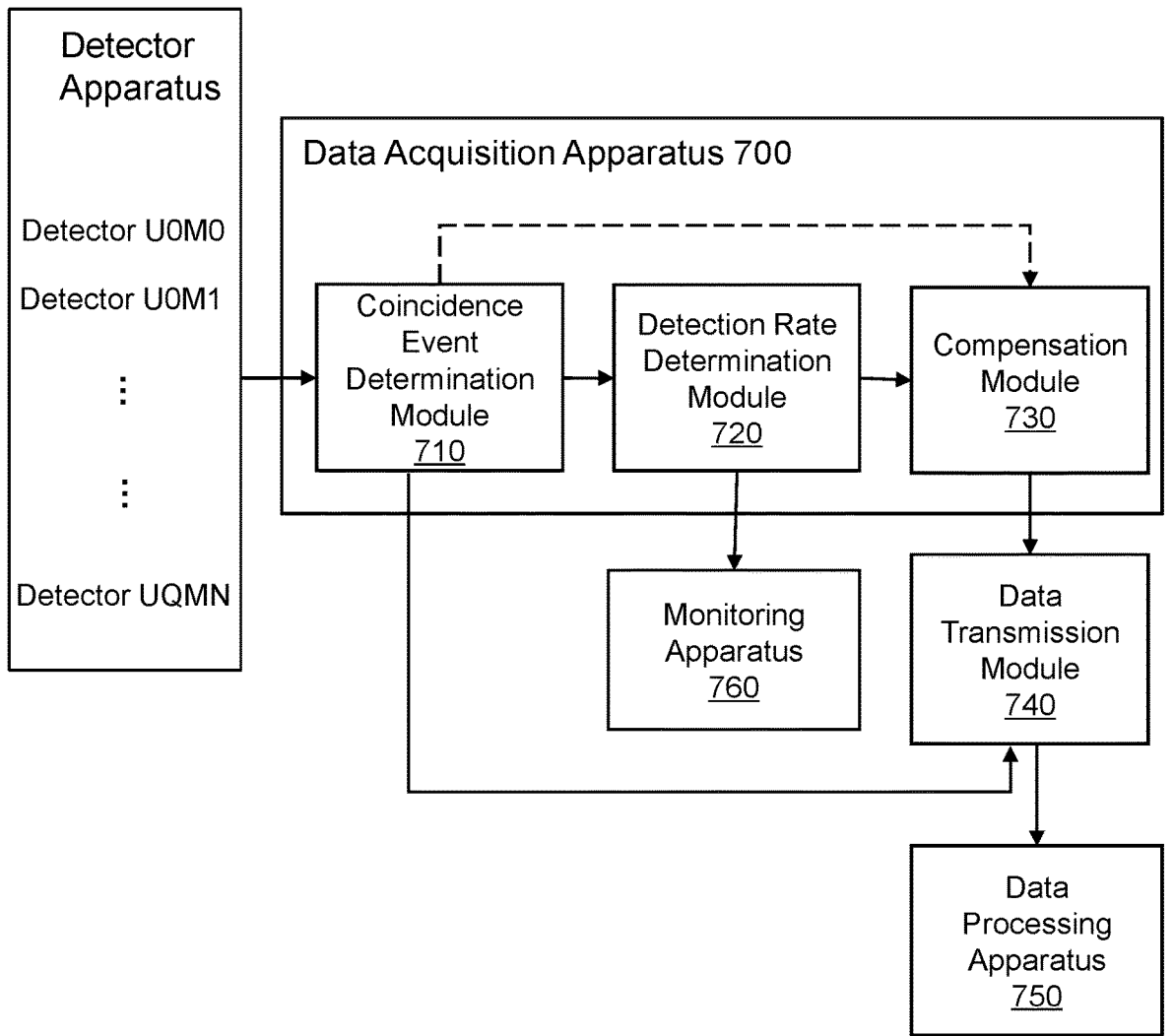
FIG. 7 is a schematic diagram illustrating another exemplary data acquisition apparatus according to some embodiments of the present disclosure.

FIG. 7 is a schematic diagram illustrating another exemplary data acquisition apparatus according to some embodiments of the present disclosure. At least a portion of process 500 may be performed by the data acquisition apparatus 700 as shown in FIG. 7. As shown in FIG. 7, the data acquisition apparatus 700 may include a coincidence event determination module 710, a detection rate determination module 720, and a compensation module 730. The coincidence event determination module 710, the detection rate determination module 720, and the compensation module 730 may be the same as or similar to the coincidence event determination module 610, the detection rate determination module 620, and the compensation module 630, respectively.

Different from the data acquisition apparatus 600, the detection rate determination module 720 may output the detection rates of the multiple LORs to a monitoring apparatus 760. The monitoring apparatus 760 may determine whether one or more target LORs exists among the multiple LORs based on the detection rates of the multiple LORs. The monitoring apparatus 760 may provide feedback in response to determining that the one or more target LORs exist among the multiple LORs. In some embodiments, each of the detection rates of the one or more target LORs may be less than the reference detection rate corresponding to each of the one or more target LORs and exceed a detection rate threshold. The detection rate threshold may be less than the reference detection rate. The detection rate threshold may be a default setting of the system or set by an operator (e.g., an engineer of the PET scanner). The monitoring apparatus 760 may provide feedback by causing the compensation module 730 to perform the compensation associated with coincidence events corresponding to the one or more target LORs. In some embodiments, the compensation module 730 may obtain the coincidence events and the detection rates of the target LORs and perform the compensation on the coincidence events based on the compensation coefficients of the target LORs as described elsewhere in the present disclosure (e.g., FIGS. 5 and 6).

In some embodiments, if the monitoring apparatus 760 determines that a detection rate of a target LOR is less than the detection rate threshold, the monitoring apparatus 760 may provide feedback associated with the target LOR. In other words, the difference between the detection rate and the reference detection rate corresponding to the target LOR is large. For example, the monitoring apparatus 760 may generate a reminder (e.g., an alarm) for the target LOR and provide the reminder to a terminal device for display. The pair of detectors may be replaced, repaired, or calibrated by an operator in response to receiving the reminder. As another example, the monitoring apparatus 760 may stop the PET scan.

In some embodiments, the monitoring apparatus 760 may cause the coincidence event determination module 710 to transmit the determined coincidence events corresponding to a portion of the multiple LORs whose detection rates are normal to the data processing apparatus 750 through the data transmission module 740. In some embodiments, the monitoring apparatus 760 may cause the coincidence event determination module 710 to transmit the determined coincidence events corresponding to the one or more target LORs whose detection rates are abnormal to the compensation module 730 for compensation.

Figure 8:
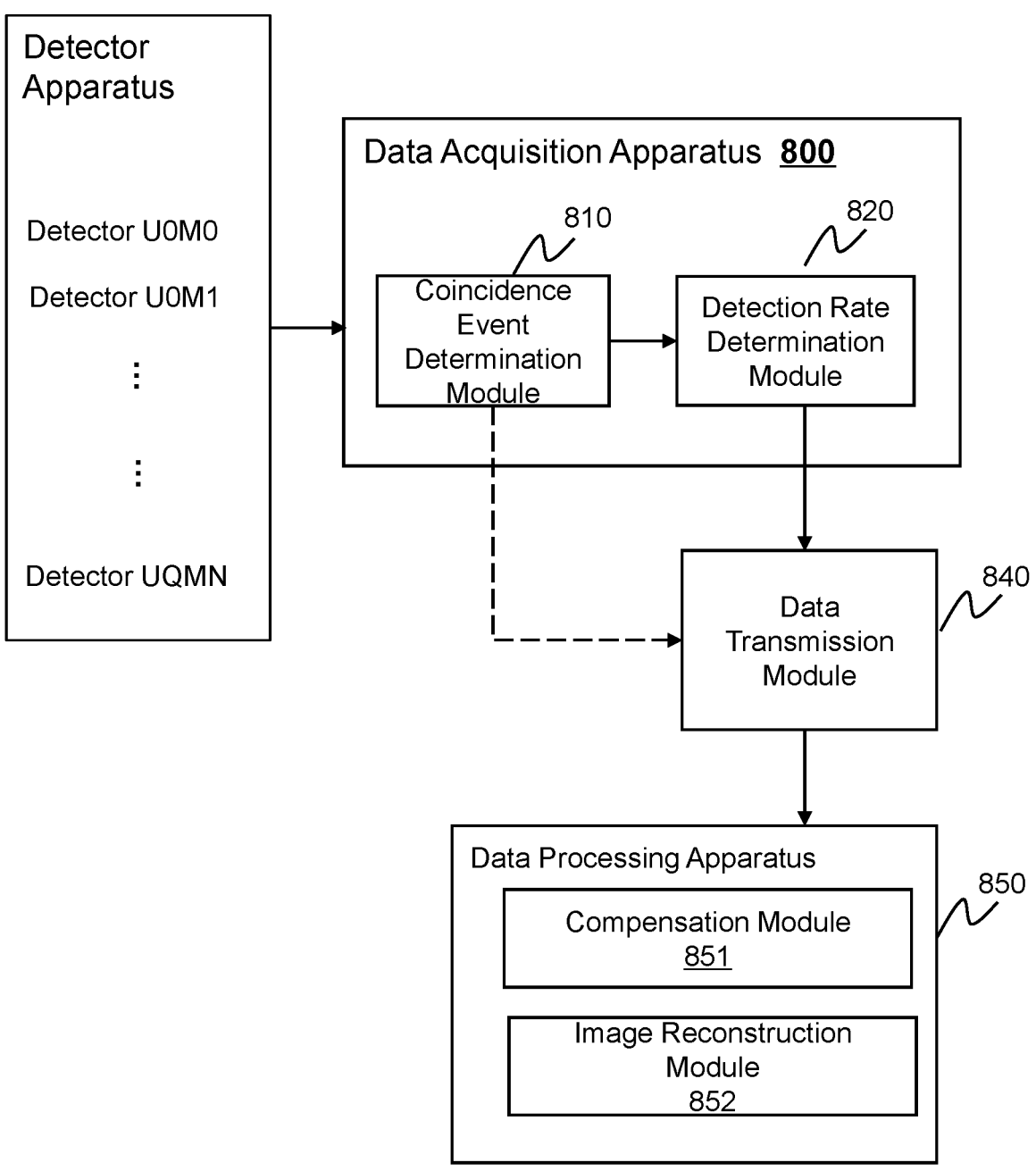
FIG. 8 is a schematic diagram illustrating another exemplary data acquisition apparatus according to some embodiments of the present disclosure.

FIG. 8 is a schematic diagram illustrating another exemplary data acquisition apparatus according to some embodiments of the present disclosure. At least a portion of process 500 may be performed by the data acquisition apparatus 800 as shown in FIG. 8. As shown in FIG. 8, the data acquisition apparatus 800 may include a coincidence event determination module 810, and a detection rate determination module 820. The coincidence event determination module 810 and the detection rate determination module 820 may be the same as or similar to the coincidence event determination module 610 and the detection rate determination module 620, respectively.

Different from the data acquisition apparatus 600, the data acquisition apparatus 800 may not include a compensation module. In some embodiments, the detection rate determination module 820 may output the coincidence events corresponding to the multiple LORs and the detection rates of the LORs to the data processing apparatus 850 through the data transmission module 840 every time period during the total time period of a PET scan of a subject. In some embodiments, the coincidence event determination module 810 may output the coincidence events corresponding to the multiple LORs to the data processing apparatus 850 through the data transmission module 840 every time period, and the detection rate determination module 820 may output the detection rates of the LORs to the data processing apparatus 850 through the data transmission module 840 every time period.

The data processing apparatus 850 may include a compensation module 851 and an image reconstruction module 852. The compensation module 851 may be the same as or similar to the compensation module 630 as described in FIG. 6. More descriptions for the compensation may be found elsewhere in the present disclosure (e.g., FIG. 6 and the descriptions thereof). The image reconstruction module 852 may reconstruct one or more PET images based on the coincidence events corresponding to the multiple LORs. The coincidence events corresponding to the multiple LORs may include compensated coincidence events corresponding to the one or more target LORs and the coincidence events corresponding to the remaining LORs among the multiple LORs excepting the one or more target LORs.

FIG. 9 is a schematic diagram illustrating another exemplary data acquisition apparatus according to some embodiments of the present disclosure. At least a portion of process 500 may be performed by the data acquisition apparatus 900 as shown in FIG. 9. As shown in FIG. 9, the data acquisition apparatus 900 may include a coincidence event determination module and a detection rate determination module. The coincidence event determination module may include a plurality of coincidence determination units (e.g., P1, P2, P3, . . . Pn). Each of the plurality of coincidence determination units may correspond to a pair of detectors along a LOR. In other words, each of the plurality of coincidence determination units may correspond to a LOR. Each of the plurality of coincidence determination units may be configured to process outputs of a pair of detectors along the corresponding LOR. The detection rate determination module may include a plurality of detection rate determination units (e.g., D1, D2, D3, . . . Dn). Each of the plurality of detection rate determination units may correspond to one of the plurality of coincidence determination units and a LOR. Each of the plurality of detection rate determination units may be configured to determine a detection rate of the LOR corresponding to the each of the plurality of detection rate determination units.

Each of the plurality of detection rate determination units may be the same as or similar to the detection rate determination module 720 or 620. Different from the detection rate determination module 720 or 620, each of the plurality of detection rate determination units may determine the detection rate of one LOR based on coincidence events generated based on the corresponding coincidence detection unit. Each of the plurality of coincidence determination units may be the same as or similar to the coincidence event determination module 710 or 610. Different from the coincidence event determination module 710 or 610, each of the plurality of coincidence determination units may determine the coincidence events of one LOR based on outputs of a pair of detectors that are in communication with the each of the plurality of coincidence determination units.

In some embodiments, the data acquisition apparatus 800 may include a compensation module (not shown). The compensation module may include a plurality of compensation units (e.g., C1, C2, C3, . . . Cn). Each of the plurality of compensation units may correspond to a pair of detectors along a LOR, one of the plurality of coincidence determination units, and one of the plurality of detection rate determination units that correspond to the LOR. Each of the plurality of compensation units may be in communication with or connected with the corresponding one of the plurality of coincidence determination units and one of the plurality of detection rate determination units. Each of the plurality of compensation units may be configured to perform compensation associated with coincidence events corresponding to the corresponding LOR. Each of the plurality of compensation units may be the same as or similar to the compensation module 730 or 630. More descriptions for the plurality of compensation units may be found elsewhere in the present disclosure (e.g., FIG. 6 and FIG. 7, and the descriptions thereof).

FIG. 10 is a schematic diagram illustrating another exemplary detection rate determination module according to some embodiments of the present disclosure. At least a portion of process 500 may be performed by the detection rate determination module 1000 as shown in FIG. 10. As shown in FIG. 10, the detection rate determination module 1000 may include a LOR determination unit 1010, a counting unit 1020, and a detection rate determination unit 1030. The LOR determination unit 1010 may be configured to determine an identity of a LOR corresponding to a coincidence event. In some embodiments, during a total time period of a PET scan of a subject, the data acquisition apparatus (e.g., the data acquisition apparatus 600 or the data acquisition apparatus 70) may determine multiple coincidence events. Each of the multiple coincidence events may correspond to a pair of photons detected by a pair of detectors along a LOR (i.e., single radiation events). Each of the multiple LORs may correspond to a pair of detectors. The LOR determination unit 1010 may be configured to determine an identity of the LOR corresponding to each of the multiple coincidence events based on the position information of the pair of detectors that detect the pair of photons. The position information of the pair of detectors may be included in the coincidence event. The position information of the pair of detectors may be denoted by serial numbers of the pair of detectors. In some embodiments, the identity of the LOR corresponding to each of the multiple coincidence events may be denoted by the position information of the pair of detectors (e.g., the serial numbers of the pair of detectors).

In some embodiments, the identity of the LOR corresponding to each of the multiple coincidence events may be denoted by a serial number (e.g., a third serial number).

In some embodiments, the LOR determination unit 1010 may determine an identity of a LOR corresponding to a coincidence event based on a LOR table. The coincidence event may include information associated with a pair of detectors (e. g., position information) that detect a pair of photons (i.e., the single radiation events) corresponding to the coincidence event. The LOR table may provide a corresponding relationship between multiple pairs of detectors (e.g., the position information) and LORs (e.g., the identities of the LORs). For example, the LOR table may provide the multiple LORs with different identities (e.g., third serial numbers) and multiple pairs of detectors with different positions (e.g., the first serial numbers and the second serial numbers). Each of the multiple LORs in the LOR table (e.g., a lookup table) may correspond to one of the multiple pairs of detectors. The LOR determination unit 1010 may determine the identity of the LOR corresponding to the coincidence event based on the position information of the pair of detectors that detect the pair of photons and the LOR table.

The counting unit 1020 may be configured to determine a count of coincidence events corresponding to a LOR that are detected based on outputs of a pair of detectors in the LOR in every time period (e.g., 1 second, 2 seconds, 10 seconds, 30 seconds, 1 minute, etc., of a total time period (e.g., 10 minutes, 20 minutes, 30 minutes, etc.) of a PET scan. As used herein, the time period when the outputs of a pair of detectors are generated or detected may be equivalent to the time period when the coincidence events are generated based on the outputs. In some embodiments, the counting unit 1020 may be configured to receive all coincidence events corresponding to the multiple LORs generated in the time period. The counting unit 1020 may determine the count of coincidence events corresponding to the LOR generated in the time period by counting coincidence events corresponding to LORs with the same identity (i.e., the same LOR). In some embodiments, the counting unit 1020 may determine an initial count (e.g., 0) of coincidence events corresponding to a LOR generated in the time period. In response to receiving a coincidence event corresponding to the LOR generated at a current time in the time period, the counting unit 1020 may update the initial count to obtain a cumulative count by adding "1." The counting unit 1020 may keep updating the cumulative count of coincidence events after receiving a coincidence event corresponding to the LOR generated in the time period, and designate the cumulative count as the count of coincidence events corresponding to the LOR until the ending time of the time period. At the beginning of the next time period, the counting unit 1020 may initialize the count of coincidence events corresponding to the LOR generated in the time period (also referred to a current time period) to obtain an initial count (e.g., 0) of coincidence events corresponding to the LOR generated in the next time period.

In some embodiments, the counting unit 1020 may include multiple counters. Each of the multiple LORs may correspond to a counter among the multiple counters. The counting unit 1020 may determine one of the multiple counters corresponding to the LOR. For example, the counting unit 1020 may include a counter table (e.g., a lookup table), and the counter table may provide a corresponding relationship between the multiple LORs and the multiple counters. The counting unit 1020 may determine a counter based on the LOR and the counter table. In some embodiments, the counter table and the LOR table may be integrated into one table. After receiving a coincidence event corresponding to the LOR and determining the counter corresponding to the LOR, the counting unit 1020 may cause the counter to update the cumulative count of coincidence events corresponding to the LOR generated in the time period until the ending of the time period. The counter corresponding to each of the multiple LORs may be initialized when the next time period begins. In other words, at the beginning of each time period, the count of coincidence events generated in each time period may be initialized to "0".

The detection rate determination unit 1030 may be configured to determine a detection rate of the LOR based on the count of coincidence events corresponding to the LOR generated in the time period. The detection rate of the LOR may be equal to a ratio of the count of coincidence events corresponding to the LOR and the length of the time period. In some embodiments, for the same LOR, different time periods may correspond to different detection rates. In some embodiments, the detection rate determination unit 1020 may output the detection rate of the LOR every time period to other modules or apparatuses for processing (e.g., the compensation module, the data processing apparatus).

It should be understood that if the coincidence events obtained at a moment in the target time period do not include time-delayed coincidence events, the processing device 140 may do not update the cumulative count of time-delayed coincidence events at the moment, that is, the cumulative count of time-delayed coincidence events at the moment is the same as the cumulative count of time-delayed coincidence events at an adjacent moment when coincidence events are obtained earlier than the moment.

What is claimed is:

1. A system, comprising:
   at least one storage device including a set of instructions; and
   at least one processor in communication with the at least one storage device, wherein when executing the set of instructions, the at least one processor is directed to cause the system to perform operations including:
   obtaining, based on outputs of multiple pairs of detectors of a Positron Emission Tomography (PET) scanner, coincidence events corresponding to multiple LORs, the outputs of the multiple pair of detectors being acquired during a PET scan on a subject;
   determining, based on a count of coincidence events corresponding to each LOR of at least a portion of the multiple LORs, a detection rate corresponding to the LOR;
   determining one or more target LORs based on a reference detection rate and the detection rate corresponding to each LOR of the at least a portion of the multiple LORs; and
   performing a compensation associated with the coincidence events corresponding to each of the one or more target LORs based on the detection rate corresponding to the target LOR.

2. The system of claim 1, wherein for each LOR of at least a portion of the multiple LORs, the operations include:
   determining the count of the coincidence events corresponding to the LOR in a time period; and
   determining the detection rate corresponding to the LOR in the time period based on the count of the coincidence events.

3. The system of claim 2, wherein each of the coincident events corresponding to the multiple LORs includes information of a pair of detectors, and the determining the count of the coincidence events corresponding to the LOR includes:

determining, based on the information of the pair of detectors included in the each of the coincidence events corresponding to the multiple LORs, identities of the multiple LORs; and determining the count of the coincidence events corresponding to the LOR by counting coincident events corresponding to LORs with the same identity of the LOR.

4. The system of claim 3, wherein the system includes multiple counters each of which corresponds to an identity of a LOR, and the determining the count of the coincidence events corresponding to the LOR includes:

determining a counter corresponding to the LOR; and obtaining the count of the coincidence events corresponding to the LOR by updating a cumulative count of the counter corresponding to the LOR at a current time until the current time is an ending time of the time period.

5. The system of claim 4, wherein the counter corresponding to the LOR is determined based on a lookup table and the identity of the LOR, the lookup table provides a relationship between identities of the multiple LORs and identities of the multiple counters.

6. The system of claim 2, wherein the operations include initializing the count of the coincidence events corresponding to the LOR at the beginning of a next time period.

7. The system of claim 1, wherein the operations include determining and outputting the detection rate corresponding to each of the at least a portion of the multiple LORs every time period.

8. The system of claim 1, wherein the determining one or more target LORs based on a reference detection rate and the detection rate corresponding to each LOR of the at least a portion of the multiple LORs include:

for each LOR of the at least a portion of the multiple LORs, comparing the detection rate corresponding to the LOR with the reference detection rate corresponding to the LOR to determine the one or more target LORs.

9. The system of claim 8, wherein the detection rate corresponding to the target LOR is less than the reference detection rate.

10. The system of claim 1, wherein the reference detection rate is determined according to operations including:

causing the PET scanner to perform a PET scan on a reference subject;

detecting reference coincidence events corresponding to each of the multiple LORs based on outputs of a pair of detectors when the PET scan is performed on the reference subject; and determining the reference detection rate based on a count of the reference coincidence events.

11. The system of claim 10, wherein the determining the reference detection rate based on the count of reference coincidence events includes:

determining candidate detection rates each of which corresponds to one of the multiple LORs based on the count of the reference coincidence events corresponding to each of the multiple LORs; and determining the reference detection rate based on the candidate detection rates.

12. The system of claim 1, wherein the reference detection rates corresponding to the at least a portion of the multiple LORs are the same.

13. The system of claim 1, wherein the operations further include:

outputting the detection rate corresponding to the each of the at least a portion of the multiple LORs to a monitoring apparatus, the monitoring apparatus being configured to provide a reminder or control in response to determining that a detection rate corresponding to a LOR is abnormal.

14. The system of claim 1, wherein the plurality of coincidence events corresponding to the LOR determined based on the outputs of the pair of detectors are generated in a target time period, wherein the target time period is a portion or a segment of the total time period of the PET scan, and the detection rate corresponding to each of at least a portion of the multiple LORs in the target time period is determined based on a count of the plurality of coincidence events corresponding to the LOR generated in the target time period.

15. The system of claim 1, wherein the performing a compensation associated with the coincidence events corresponding to each of the one or more target LORs based on the detection rate corresponding to the target LOR comprises:

determining a compensation coefficient corresponding to the target LOR based on the reference detection rate and the reference rate of the target LOR;

duplicating a portion of the coincidence events corresponding to the target LOR based on the compensation coefficient corresponding to the target LOR.

16. The system of claim 1, further comprising:

obtaining compensated coincidence events corresponding to one or more target LORs; and reconstructing one or more PET images based on the compensation coincidence events corresponding to the one or more target LORs and coincidence events corresponding to one or more remaining LORs among the multiple LORs excepting the one or more target LORs.

17. The system of claim 1, wherein the PET scanner includes an electronics assembly supported by a gantry of the PET scanner, and an apparatus for data acquisition is included in the electronics assembly.

18. A method implemented on a computing device including at least one processor and a storage device, the method comprising:

obtaining, based on outputs of multiple pairs of detectors of a Positron Emission Tomography (PET) scanner, coincidence events corresponding to multiple LORs, the outputs of the multiple pair of detectors being acquired during a PET scan on a subject;

determining, based on a count of coincidence events corresponding to each LOR of at least a portion of the multiple LORs, a detection rate corresponding to the LOR;

determining one or more target LORs based on a reference detection rate and the detection rate corresponding to each LOR of the at least a portion of the multiple LORs; and performing a compensation associated with the coincidence events corresponding to each of the one or more target LORs based on the detection rate corresponding to the target LOR.

19. The method of claim 18, wherein for each LOR of at least a portion of the multiple LORs, the method includes:

determining the count of the coincidence events corresponding to the LOR in a time period; and determining the detection rate corresponding to the LOR in the time period based on the count of the coincidence events.

20. A non-transitory computer readable medium, comprising at least one set of instructions, wherein when executed by one or more processors of a computing device, the at least one set of instructions causes the computing device to perform a method, the method comprising:

obtaining, based on outputs of multiple pairs of detectors of a Positron Emission Tomography (PET) scanner, coincidence events corresponding to multiple LORs, the outputs of the multiple pair of detectors being acquired during a PET scan on a subject;

determining, based on a count of coincidence events corresponding to each LOR of at least a portion of the multiple LORs, a detection rate corresponding to the LOR;

determining one or more target LORs based on a reference detection rate and the detection rate corresponding to each LOR of the at least a portion of the multiple LORs; and performing a compensation associated with the coincidence events corresponding to each of the one or more target LORs based on the detection rate corresponding to the target LOR.

\* \* \* \* \*